United States Patent [19]
Bielefeldt

[11] Patent Number: 5,455,376
[45] Date of Patent: Oct. 3, 1995

[54] PROCESS FOR THE PREPARATION OF ALIPHATIC OMEGA-DIFLUOROCARBOXYL COMPOUNDS

[75] Inventor: Dietmar Bielefeldt, Ratingen, Germany

[73] Assignee: Bayer Aktiengesellschaft, Leverkusen, Germany

[21] Appl. No.: 347,994

[22] Filed: Dec. 5, 1994

[30] Foreign Application Priority Data

Dec. 10, 1993 [DE] Germany .......................... 43 42 187.3

[51] Int. Cl.$^6$ .......................... C07C 51/00; C07C 69/63
[52] U.S. Cl. .............................. 562/604; 560/227
[58] Field of Search .............................. 562/604; 560/227

[56] References Cited

U.S. PATENT DOCUMENTS

| | | | |
|---|---|---|---|
| 2,863,917 | 12/1958 | Rucker et al. | 562/604 |
| 3,071,615 | 1/1983 | Opitz et al. | 562/604 |
| 5,191,118 | 3/1993 | Coiveia et al. | 562/604 |

FOREIGN PATENT DOCUMENTS

| | | |
|---|---|---|
| 645929 | 7/1962 | Canada . |
| 910778 | 7/1949 | Germany . |
| 3048229 | 2/1988 | Japan . |
| 1045447 | 12/1986 | United Kingdom . |

OTHER PUBLICATIONS

Collection of Czechoslovak Chemical Compounds, vol. 351, No. 4, Apr. 1970 pp. 1302–1306.

*Primary Examiner*—Paul J. Killos
*Attorney, Agent, or Firm*—William C. Gerstenzang; Sprung Horn Kramer & Woods

[57] ABSTRACT

Aliphatic ω-difluorocarboxyl compounds are prepared in an economic manner from aliphatic ω-monohalogeno-difluorocarboxyl compounds by bringing the latter into contact with hydrogen in the presence of a catalyst which is applied to an inert support material and comprises one or more metals of group VIII of the Periodic Table at 120° to 250° C.

10 Claims, No Drawings

PROCESS FOR THE PREPARATION OF ALIPHATIC OMEGA-DIFLUOROCARBOXYL COMPOUNDS

The present invention relates to an economic preparation process for aliphatic ω-difluorocarboxyl compounds from the corresponding ω-monohalogeno-difluoro-carboxyl compounds.

Difluoroacetic acid is an intermediate product for the preparation of plant protection agents. For example, it is required for the preparation of 5-difluoromethyl-1,3,4-thiazol-2-yloxy derivatives (see DE-A1 38 21 597). Longer-chain fluorinated alkanecarboxylic acids and salts thereof are known as surface-active substances and can be employed as emulsifiers in the polymerization of fluorinated monomers (see Ullmann's Encyclopedia of Industrial Chemistry, Volume All, page 371 et seq. (1988)).

Difluoroacetic acid can be synthesized from secondary products of tetrafluoroethene or by oxidation of 3,3'-difluoropropenes with potassium permanganate (see, for example, J. Amer. Chem. Soc. 74, 1426 (1952) and J. Amer. Chem. Soc. 71, 343 (1949) and the literature cited there). Both preparation methods are not of particular economic interest. In particular, in the first process mentioned, the starting substances are accessible only with difficulty, and in the process mentioned last, there is the problem of disposal of the manganese hydroxides and manganese oxides formed.

A process has now been found for the preparation of ω-difluorocarboxyl compounds of the formula (I)

in which
n represents zero or an integer from 1 to 5 and
R represents hydrogen, $C_1$–$C_{10}$-alkyl, $C_5$–$C_7$cycloalkyl, $C_6$–$C_{10}$-aryl or $C_7$–$C_{12}$-aralkyl,
which is characterized in that a difluorocarboxyl compound of the formula (II)

in which
X represents chlorine, bromine or iodine and
n and R have the meaning given in the case of formula (I)
,
is brought into contact with hydrogen in the presence of a catalyst which is applied to an inert support material and comprises one or more metals of group VIII of the Periodic Table at 120° to 250° C.

In formula (II), X preferably represents chlorine, n preferably represents zero, 1 or 2 and R preferably represents hydrogen or $C_1$–$C_4$-alkyl. Accordingly, difluorocarboxyl compounds of the formula (I) in which n represents zero, 1 or 2 and R represents hydrogen or $C_1$–$C_4$-alkyl are preferably prepared by the process according to the invention. Difluoroacetic acid is especially preferably prepared according to the invention from monochloro-difluoro-acetic acid.

The starting substances of the formula (II) are commercially obtainable or can be prepared in a simple manner and in a manner known in principle, for example from carbon tetrachloride, an olefin and carbon monoxide (see J. org. Chem. 35, 2982 (1970)) and subsequent fluorination with HF (see M. Hudlichy, Chemistry of Organic Fluorine Compounds, New York (1972)).

Commercially available hydrogen can be employed as the hydrogen. 1 to 100 mol of hydrogen, for example, can be employed per g-atom of X contained in the compound of the formula (II) employed. This amount is preferably in the range from 2 to 50 mol.

The catalysts to be employed in the process according to the invention can comprise as metals, for example, palladium, platinum and/or nickel. The metals can be present as such or in the form of compounds. Palladium in elemental form is preferred. Preferred support materials are aluminium oxide and lithium aluminium spinel. The catalysts can comprise, for example, 0.01 to 10 % by weight of metal, calculated as metal. This amount is preferably 0.1 to 2% by weight. If appropriate, the catalysts can be doped with other main group and/or sub-group metals and/or compounds of main group and/or sub-group metals. Examples of such dopings are salts of lead, silver, indium, vanadium and thallium. The dopings can be present, for example, in amounts of 0.1 to 100% by weight, based on the metal or metals of group VIII of the periodic table.

The process according to the invention can be carried out under the most diverse pressures, for example under 0.1 to 16 bar. Pressures in the range from 1 to 5 bar are preferred, and normal pressure is particularly preferred. The reaction temperature is preferably in the range of 150°–200° C. The pressure and temperature are preferably coordinated with one another such that the particular compound of the formula (II) employed comes into contact with the catalyst in gaseous form.

10 to 2000 g per hour, for example, of a compound of the formula (II) can be passed over one liter of the catalyst. The catalyst loading is preferably 50 to 500 g/1× hour. The reaction can also be carried out in the presence of inert gases.

The mixture leaving the reaction space can be worked up, for example, by first condensing the condensable portions and isolating the compound of the formula (I) prepared by subjecting the condensate to fractional distillation.

Unreacted starting substance and excess hydrogen can be employed again in the process according to the invention.

The process according to the invention has a number of advantages. A fairly pure product can be obtained in a simple and economic manner. The conversions and/or selectivites which can be achieved are high. Essentially one gaseous by-product (hydrogen halide) is formed, which can be separated off in a simple manner.

It is surprising that the halogen can be split off selectively from a monohalogeno-difluoro starting compound by the process according to the invention without fluorine atoms being noticeably split off.

EXAMPLES

General working instructions:

A perpendicular, heatable quartz tube with a hydrogen feed was filled with 200 ml of the particular catalyst stated. The monochloro-difluoro-acetic acid was metered in via a metering pump and the hydrogen was metered in via a rotameter. After the catalyst had been flushed with nitrogen under normal pressure and dried, the monochloro-difluoro-acetic acid and the hydrogen (both gaseous) were passed through the quartz tube in the particular amounts stated at the particular temperature stated. The reaction mixture leaving the quartz tube was condensed at −78° C. and then distilled. At least 98% pure products were thus obtained, and can be reacted further without further purification.

Catalysts employed:

A 5 g of palladium per liter of aluminiumoxide, doped with 0.25% by weight of silver nitrate (based on palladium).

5 g of palladium per liter of aluminiumoxide, doped with 0.25% by weight of thallium(I) nitrate (based on the palladium).

C 5 g of palladium per liter of aluminium oxide.

D 18 g of palladium per liter of lithium aluminium spinel.

E As D, but doped with 60% by weight of vanadium oxide and 30.5% by weight of lead diacetate (in each case based on the palladium).

Details of the examples carried out can be seen from the following table.

| Example No. | Catalyst | Temperature [°C.] | Loading [g/l × h] | Molar ratio of $H_2$: educt | Conversion [%] | Selectivity [%] |
|---|---|---|---|---|---|---|
| 1 | A | 150 | 130 | 22.3 | 33 | 79 |
| 2 | A | 150 | 130 | 11.1 | 9.6 | 86 |
| 3 | B | 200 | 130 | 22.3 | 39 | 86 |
| 4 | C | 150 | 130 | 22.3 | 43 | 91 |
| 5 | C | 250 | 130 | 22.3 | 99 | 32 |
| 6 | D | 200 | 25 | 65 | 80 | 83 |
| 7 | D | 150 | 25 | 65 | 61 | 78 |
| 8 | D | 150 | 91 | 12.7 | 64 | 73 |
| 9 | D | 150 | 79 | 14.8 | 51 | 90 |
| 10 | E | 150 | 136 | 15 | 95 | 95 |
| 11 | E | 175 | 136 | 14.9 | 99 | 99 |

What is claimed is:

1. A process for the preparation of a ω-difluorocarboxyl compound of the formula (I)

$$CF_2H\text{---}(CH_2)_n\text{---}CO_2R \qquad (I),$$

in which n represents zero or an integer from 1 to 5 and

R represents hydrogen, $C_1$–$C_{10}$-alkyl, $C_5$–$C_7$-cycloalkyl, $C_6$–$C_{10}$-aryl or $C_7$–$C_{12}$-aralkyl, comprising that a difluorocarboxyl compound of the formula (II)

$$CF_2X\text{---}(CH_2)_n\text{---}CO_2R \qquad (II),$$

in which

X represents chlorine, bromine or iodine and n and R have the meaning given in the case of formula (I), is brought into contact with hydrogen at 120° to 250° C. in the presence of a catalyst which is applied to an inert support material and comprises one or more metals of group VIII of the Periodic Table.

2. The process according to claim 1, in which in the formulae (I) and (II), n represents zero, 1 or 2 and R represents hydrogen or $C_1$–$C_4$-alkyl, and in formula (II), X represents chlorine.

3. The process of claim 1, in which 1 to 100 mol of hydrogen are employed per g atom of X contained in the compound of the formula (II) employed.

4. The process of claim 1, in which the catalyst comprises palladium, platinum and/or nickel in metallic form or in the form of compounds and, as the support material, aluminium oxide or lithium aluminium spinel.

5. The process of claim 1, in which the catalyst comprises 0.01 to 10% by weight of metal.

6. The process of claim 1, in which the catalyst is additionally doped with other main group and/or sub-group metals and/or compounds of main group and/or sub-group metals.

7. The process of claim 1, in which it is carried out at 150° to 200° C. under pressures in the range from 0.1 to 16 bar.

8. The process of claim 1, in which the pressure and temperature are coordinated with one another such that the particular compound of the formula (II) employed comes into contact with the catalyst in gaseous form.

9. The process of claim 1, in which 10 to 2000 g per hour of a compound of the formula (II) are passed over one liter of the catalyst.

10. The process of claim 1, in which the mixture leaving the reaction space is worked up by condensing the condensable portions isolating the compound of the formula (I) prepared by subjecting the condensate to fractional distillation.

* * * * *